US011903799B2

(12) United States Patent
Mabey et al.

(10) Patent No.: US 11,903,799 B2
(45) Date of Patent: Feb. 20, 2024

(54) SEMI-RIGID BANDAGE

(71) Applicants: Brent Edward Mabey, Salt Lake City, UT (US); Jennifer Bowen, Millcreek, UT (US)

(72) Inventors: Brent Edward Mabey, Salt Lake City, UT (US); Jennifer Bowen, Millcreek, UT (US)

( * ) Notice: Subject to any disclaimer, the term of this patent is extended or adjusted under 35 U.S.C. 154(b) by 176 days.

(21) Appl. No.: 17/510,559

(22) Filed: Oct. 26, 2021

(65) Prior Publication Data

US 2022/0125644 A1 Apr. 28, 2022

Related U.S. Application Data

(60) Provisional application No. 63/106,005, filed on Oct. 27, 2020.

(51) Int. Cl.
| | |
|---|---|
| *A61F 5/00* | (2006.01) |
| *A61F 13/04* | (2006.01) |
| *A61L 15/12* | (2006.01) |
| *A61F 5/30* | (2006.01) |
| *A61F 13/00* | (2006.01) |

(52) U.S. Cl.
CPC ............... *A61F 13/04* (2013.01); *A61F 5/30* (2013.01); *A61L 15/12* (2013.01); *A61F 2013/00336* (2013.01); *A61L 2300/402* (2013.01); *A61L 2300/404* (2013.01); *A61L 2300/418* (2013.01)

(58) Field of Classification Search
None
See application file for complete search history.

(56) References Cited

U.S. PATENT DOCUMENTS

| | | | | | |
|---|---|---|---|---|---|
| 4,793,330 | A | * | 12/1988 | Honeycutt | A61F 13/04 523/105 |
| 4,968,542 | A | * | 11/1990 | Gasper | A61L 15/12 602/8 |
| 7,172,565 | B2 | * | 2/2007 | Termanini | A61F 13/04 602/8 |
| 8,343,082 | B2 | * | 1/2013 | Evans | A61F 13/06 602/8 |

FOREIGN PATENT DOCUMENTS

| | | | | | |
|---|---|---|---|---|---|
| JP | | 559246 A | * | 3/1993 | ............ A61L 15/12 |
| WO | WO-0050094 A1 | * | 8/2000 | ............ A61L 15/12 |

OTHER PUBLICATIONS

Shivamurthy et al., Comparison of octyl-2-cyanoacrylate and conventional sutures in facial skin, 2010, National Journal of Maxillofacial Surgery, v.1(1): Jan.-Jun. 2010 https://www.ncbi.nlm.nih.gov/pmc/articles/PMC3304180/ (Year: 2010).*

* cited by examiner

*Primary Examiner* — Kim M Lewis
(74) *Attorney, Agent, or Firm* — Workman Nydegger

(57) ABSTRACT

Semi-rigid bandages disclosed herein include a bandage structure layer with an embedded resin material. The resin material is formulated to cure when exposed to an activator such as air or water. Upon curing, the bandage hardens to a semi-rigid state that is harder and more rigid than conventional bandage materials found in household first-aid kits, yet less rigid than fiberglass-based orthopedic casts.

19 Claims, 5 Drawing Sheets

SEMI-RIGID BANDAGE

CROSS-REFERENCE TO RELATED APPLICATIONS

This application claims priority to and the benefit of U.S. Provisional Application No. 63/106,005, filed Oct. 27, 2020 and titled "Semi-Rigid Bandage". The entirety of the foregoing application is incorporated herein by this reference.

BACKGROUND

Technical Field

This disclosure generally relates to wound and injury management. In particular, this disclosure relates to bandages and dressings configured to harden into a semi-rigid state following desired placement, and which are useful in tissue and joint applications for both animals and humans.

Related Technology

Wound and injury management has conventionally involved the use of relatively soft bandages such as common adhesive bandages (e.g., Band-Aid®), gauze, and dressing wraps (e.g., ACE® wraps). These types of care products are widely available and easily purchased, and are therefore commonly utilized for at-home use and commonly found in first-aid kits. The prevalence of these types of soft bandages means they are also widely stocked and used in medical practices and hospitals as well.

While these types of soft bandages can be effective for a variety of minor wounds and injuries, more severe injuries such as broken bones and/or deep lacerations usually require other means of care. For example, broken bones often require the placement of an orthopedic cast to allow the affected bone to be properly set and isolated as it heals. Orthopedic casts were traditionally made by coating a fabric material in calcined gypsum (i.e., Plaster of Paris) and wetting the material to begin the setting process. Modern orthopedic casts usually consist of an inner fabric wrap and an exterior fiberglass wrap impregnated with a polyurethane formulated to cure upon wetting. Orthopedic casts are very rigid and require the use of specialized cutting tools for removal.

As another example, severe lacerations often require the use of surgical suture or "stitches" to sew the wound shut. On some occasions a tissue glue, usually cyanoacrylate based, may be used along with stitching or as an alternative to stitching for wound closure. While these techniques can be effective, it is not uncommon for the associated wound to be subsequently aggravated or even reopened as a result of bumping of the wound or strain placed on the wound.

While the above-described types of wound and injury management products have provided many benefits, several limitations remain. The soft and pliable products available from the store for at-home and common first-aid use are often lacking in desired levels of structure and rigidity. For example, someone with a sprained ankle or wrist may wrap the affected joint using a common elastic bandage/dressing. While this can provide compression and limited support to the affected joint, it does not provide much additional orthopedic support. On the other hand, these types of injuries do not justify the use of a full orthopedic cast, which would be overly rigid and could not be easily applied and removed when convenient.

As another example, someone may have a cut that is somewhat too severe to be appropriately closed using standard adhesive bandages, gauze, or dressings. These cuts usually require stitching and its accompanying inconveniences. This can be particularly frustrating for cuts that are not severe, but still too large or deep to be appropriately handled with standard first-aid bandaging.

Accordingly, there is an ongoing need for wound and injury management products capable of addressing issues such as those described above. In particular, there remains a need for bandages capable of providing greater support and structure than the standard adhesive bandages and dressings commonly available in the store and in first-aid kits, but not having the excessive rigidity of orthopedic cast materials. There also remains a need for products that can provide these benefits without the inconveniences and complexities of products that must be applied in a medical setting as with orthopedic casts and stitches.

SUMMARY

Embodiments of the present disclosure are directed to semi-rigid bandage materials and semi-rigid bandages made therefrom. The semi-rigid bandages described herein are designed to be flexible and pliable when in an uncured position, such that they can be easily manipulated, shaped, and wrapped as desired for placement at a wound or injury site, and then to harden into a "semi-rigid" state after exposure to a curing agent (e.g., air, water, or chemical). Such semi-rigid bandages may be utilized in tissue and/or joint applications.

The semi-rigid bandages described herein provide various degrees of rigidity that are greater than that of standard adhesive bandages or dressings, but less than that of conventional fiberglass orthopedic casts. For example, semi-rigid bandages are designed to be rigid and hard enough that the user cannot simply tear or unwrap them, but soft enough to be cut with handheld scissors (e.g., general household or medical specialty scissors) without great difficulty.

The semi-rigid bandages described herein fill a long felt need in the art of wound and injury management products. The semi-rigid bandages provide greater support, structure, and stability than standard household and first-aid bandage materials, but are less rigid than orthopedic casts. The semi-rigid bandages therefore allow for treatment of wounds and injuries that are not well served by standard bandage materials, but that are not so severe that they require casting. The semi-rigid bandages described herein may be utilized for community/household injury management or prevention and for professional (e.g., doctor's office, emergency room) injury management and prevention.

In one embodiment, the semi-rigid bandage material includes a bandage structure layer and a curable resin material embedded within the bandage structure layer. The curable resin material is formulated to cure and thereby form the semi-rigid bandage. The semi-rigid bandage material may further include a padding layer disposed on a side of the bandage structure layer. The semi-rigid bandage material may also include one or more embedded components such as a clotting factor, antimicrobial, analgesic, or anesthetic agent.

In one embodiment, a kit includes the semi-rigid bandage material and one or more of an activator in a container, a tissue glue in a dispenser, and a cutting tool. The activator may be sterile water (e.g., sterile saline), for example, provided in a pouch or other container. The cutting tool may be provided as a pair of round-tip scissors. Preferably, the cutting tool has a blade with a height that is no greater than a thickness of the padding layer so that the user can readily insert the cutting blade into the padding layer between the skin and the bandage structure layer to begin cutting the semi-rigid bandage.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Overview of Semi-Rigid Bandages

The present disclosure relates to semi-rigid bandage materials and semi-rigid bandages made therefrom. The semi-rigid bandages described herein are designed to be flexible and pliable when in an uncured position, such that they can be easily manipulated, shaped, and wrapped as desired for placement at a wound or injury site, and then to harden into a "semi-rigid" state after exposure to a curing agent (e.g., air or water).

As explained in greater detail below, the term "semi-rigid" is used herein to describe a level of rigidity greater than that of standard adhesive bandages or dressings, but less than that of conventional fiberglass orthopedic casts. For example, semi-rigid bandages are designed to be rigid and hard enough that the user cannot simply tear or unwrap them, but soft enough to be cut with general household scissors without great difficulty.

Figure 1A:
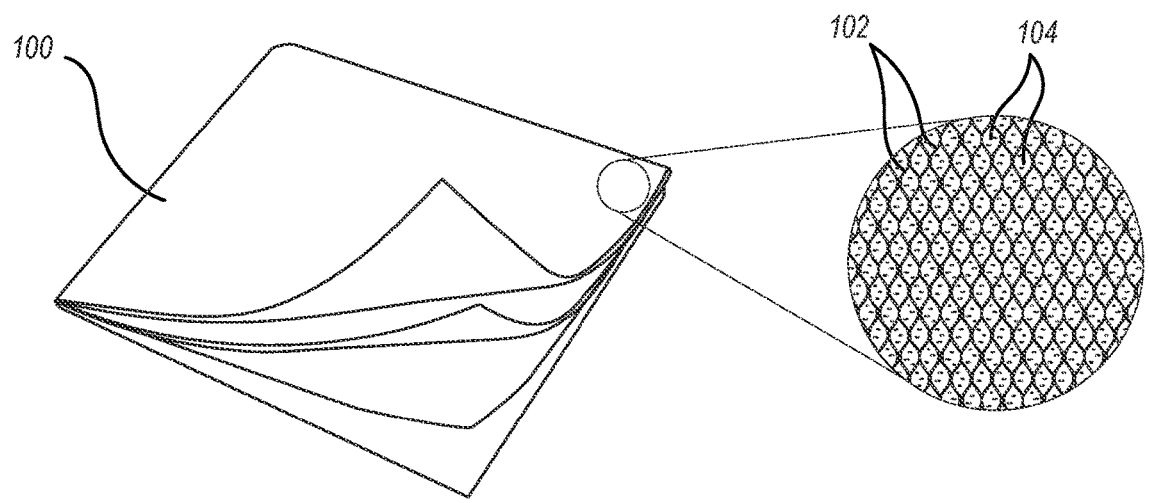
FIG. 1A illustrates an embodiment of a semi-rigid bandage material having a bandage structure layer and a curable resin material embedded therein.

FIG. 1A illustrates an example of a semi-rigid bandage material 100. The semi-rigid bandage material 100 may be provided in the form of a gauze, fabric, mesh, or the like. Any suitable soft bandage material, or combination thereof, as known in the art may be utilized in the semi-rigid bandage material 100. Examples, include cotton, polyester, rayon, and blends thereof. In some embodiments, the semi-rigid bandage material 100 includes a self-adhering material such as Coban™. The semi-rigid material preferably omits materials such as fiberglass that would contribute to excessive rigidity once the bandage has set. The semi-rigid bandage material 100 may be woven or non-woven in construction.

FIG. 1A also illustrates, in the zoomed-in section, a curable resin material 104 embedded within the bandage structure layer 102. The curable resin material 104 is configured to harden/cure upon exposure to one or more activation agents. For example, the resin 104 may be formulated to begin polymerization upon exposure to air and/or water. In such embodiments, the semi-rigid bandage material 100 may be packaged in a way that prevents exposure to air and moisture. The user can begin the curing process by opening the packaging (for air activated embodiments) and adding water (for water activated embodiments). Some resins 104 are technically water activated, but are sensitive enough to moisture in the air that they are functionally activated upon exposure to air. Once cured, the resin 104 imparts the beneficial semi-rigid properties to the material 100.

The resin material 104 may include any suitable material known in the art capable of hardening the bandage structure layer 102 to a semi-rigid state. Preferred embodiments include a polyurethane prepolymer, though other embodiments may additionally or alternatively include other thermoset polymers capable of polymerizing in the presence of an available, convenient activator such as air or water. Examples include cyanoacrylate esters and epoxy resins with silane group termini, such as trialkoxy- or trihalo-silane group termini. The resin material 104 may also include one or more catalysts, stabilizers, and/or other components to aid in curing.

The semi-rigid bandage material 100 may also include one or more additional impregnated additives such as analgesics, anesthetics (e.g., lidocaine), clotting factors, and/or antimicrobial compositions. Exemplary antimicrobial compositions include silver, iodine, chlorhexidine, bacitracin, polymyxin B, organic acids such as acetic acid, polyhexamethyl-biguanide (PHMB), permanganate salts, other suitable antiseptics, other antimicrobial formulations, and combinations thereof.

Figure 1B:
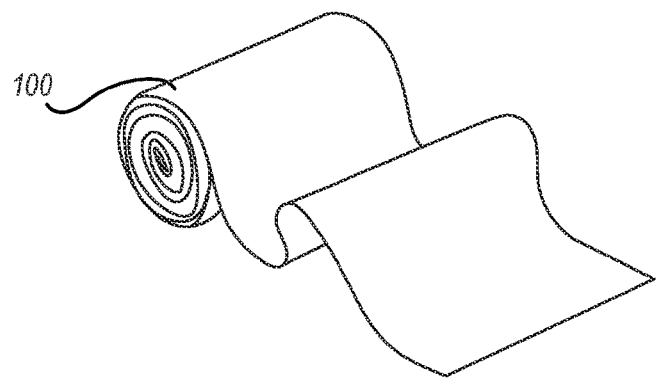
FIG. 1B illustrates the semi-rigid bandage material in a rolled gauze configuration.

The semi-rigid bandage material 100 may be provided in a folded form, rolled form, or other suitable form. FIG. 1B, for example, illustrates the semi-rigid bandage material 100 provided as a roll. In some embodiments, the semi-rigid bandage material 100 may incorporate adhesive backings such as with common adhesive bandages. In some embodiments, the semi-rigid bandage material 100 may include elastomeric materials to increase the overall elastic property to the material, such as common to many dressing wraps.

The bandage structure layer 102 and resin material 104 are selected and configured so that the resulting semi-rigid bandage material 100 is capable of hardening to a semi-rigid state. As described above, a semi-rigid state refers to a state that is more rigid and hard that standard household bandaging and wraps, but less than a fiberglass-based orthopedic cast. The semi-rigid bandage cannot be easily torn, peeled, or unwrapped by the user, but is readily cuttable with household scissors without great difficulty.

As an example, the semi-rigid bandage material 100, when cured, may have a Shore A hardness of about 40 to about 100, or about 50 to about 90, or about 60 to about 80. As another example, the semi-rigid bandage material 100, when cured, may have a Young's modulus of about 0.5 to about 3.5 GPa, or about 1 to 3 GPa, or about 1.5 to 2.5 GPa. In functional terms, the semi-rigid bandage material 100, when cured, has a hardness and/or Young's modulus between a conventional dressing wrap (e.g., ACE® wrap) and a conventional orthopedic cast. The foregoing ranges are presently believed to cover embodiments that meet this functional requirement. However, other embodiments may have hardness and/or Young's modulus values that lie outside these ranges yet still meet the functional requirement of being between a conventional dressing wrap and a conventional orthopedic cast.

Figure 2:
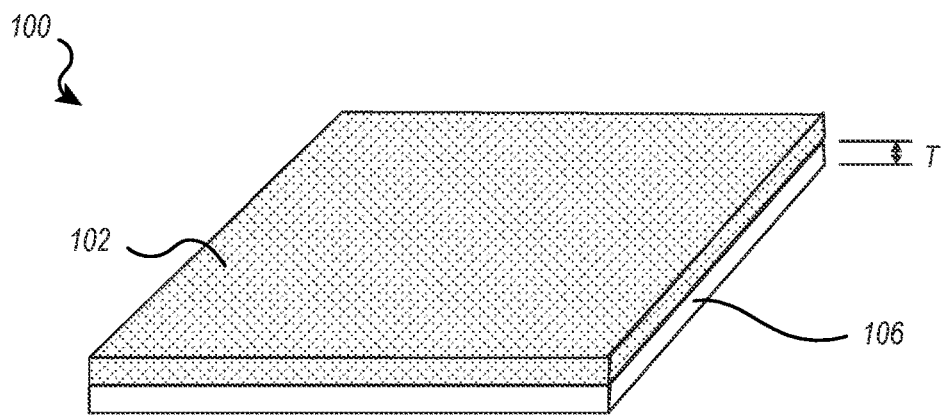
FIG. 2 illustrates the semi-rigid bandage material in a configuration that includes a padding layer.

FIG. 2 illustrates the semi-rigid bandage material 100 in a configuration that includes a padding layer 106. As shown, padding layer 106 may be disposed on or attached to one side of the bandage structure layer 102. The padding layer 106 is intended to be on the side of the semi-rigid bandage material 100 that contacts the skin and/or wound of the user. The padding layer 106 may be formed from a fabric material or other suitable material capable of providing comfortable padding to the user. It may be formed of a material different from the material of the bandage structure layer 102. In other embodiments, it may be formed from the same material as the bandage structure layer 102. The padding layer 106, however, preferably omits embedded resin 104 and thus does not harden into a semi-rigid state but retains its original pliability and softness.

The padding layer 106 has a thickness "T" that may or may not be equal to a thickness of the bandage structure layer 102. The thickness T may be, for example, about $1/16^{th}$ of an inch to about $1/2$ of an inch, but preferably about $1/8^{th}$ of an inch to about $3/8^{th}$ of an inch. As described more below, the thickness T may be set to be at least as much as a blade height of a corresponding set of scissors or other cutting tool. This allows the user to readily place the blade between the hardened bandage structure layer 102 and the skin surface when the user desires to remove the semi-rigid bandage 100.

Exemplary Uses

FIGS. 3A through 3D illustrate various exemplary uses of the semi-rigid bandage material 100. Common uses may include using the semi-rigid bandage material 100 to add support to an injured joint, such as a sprained ankle, wrist, finger, toe, or other injured joint. Other common uses include using the semi-rigid bandage material 100 as bandaging for a cut or laceration. The following examples may relate to specific uses and specific body parts, but it will be understood that the semi-rigid bandage material 100 is not restricted to only the following uses.

The semi-rigid bandage material 100 may be applied in a circumferential manner (i.e., so as to wrap completely around the affected area) or in a non-circumferential manner (i.e., as a patch, strip, or other shape that does not wrap completely wrap around the affected area). The padding layer 106 may be particularly beneficial for circumferential applications where there is greater concern that an overly tight bandage could cut off circulation. However, use of a padding layer 106 is not restricted to circumferential applications only.

Figure 3A:
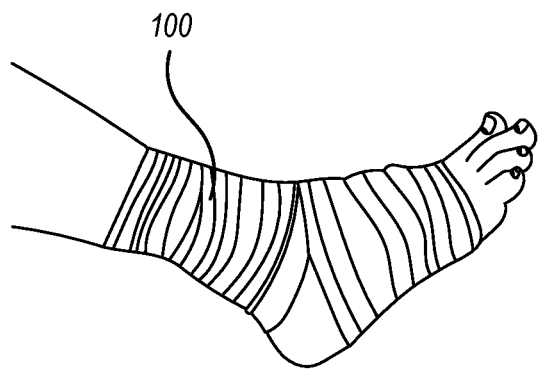
FIGS. 3A through 3L illustrate various exemplary uses of the semi-rigid bandage material.
Figure 3B:
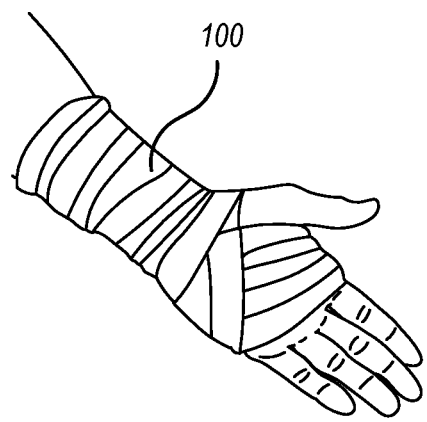

As shown in FIGS. 3A and 3B, the semi-rigid bandage material 100 may be applied as a supporting wrap to an affected area of the body, including a joint such as the ankle or wrist, or other parts of the hand or foot, for example. When used in this manner, the semi-rigid bandage material 100 can beneficially provide greater support to the affected area than a standard, soft dressing. The semi-rigid bandage material 100 is conveniently applied in the same manner as a standard, soft dressing, but hardens to a semi-rigid state that supports joint sprains and other injuries.

The semi-rigid bandage material 100 may also be applied to a target site to prevent injury at the target site. For example, the semi-rigid bandage material 100 may be applied to the ankles, hands, and/or wrists of a user prior to athletic activities (e.g., football, basketball, soccer, boxing, horse riding, etc.) or other activities where injury prevention is desired.

Figure 3C:
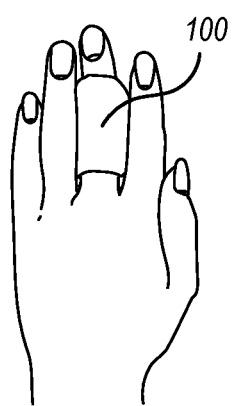
Figure 3D:
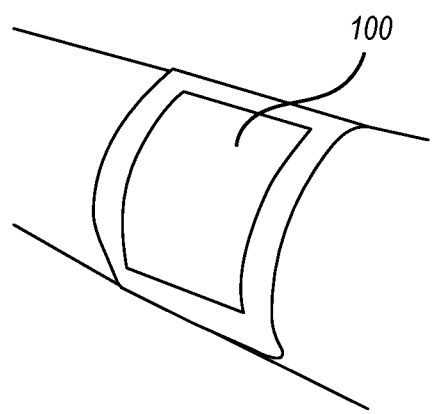

FIG. 3C illustrates the semi-rigid bandage material 100 applied around a finger. Such an application may be useful where the finger is sprained (i.e., "jammed") and/or where there is a cut or laceration on the finger. FIG. 3D illustrates an application where the semi-rigid bandage material 100 is applied in a non-circumferential manner to cover a wound such as a cut or laceration.

In some instances, the semi-rigid bandage material 100 may be used as an alternative to stitching. For example, some cuts or lacerations may not be so immediately serious that a trip to the emergency room is apparent, but may still be difficult to properly close with conventional household and first-aid bandages. In the past, such injuries often required stitching simply because there were limited alternatives available. However, many of these types of injuries may be effectively treated using the semi-rigid bandage material 100 and the need for stitching may therefore be reduced. The semi-rigid property of the bandage 100 provides greater strength and structural support to better maintain closure of these types of cuts.

Moreover, even in instances where stitching is recommended or cannot be avoided, the semi-rigid bandage material 100 can be applied on top of the sutured injury site. The resulting semi-rigid bandage beneficially functions to protect the wound and the sutures from unintentional bumps and strain that can aggravate or even re-open the wound. The semi-rigid bandage can also function to limit exposure of the wound and the sutures to sources of infection.

Figure 3E:
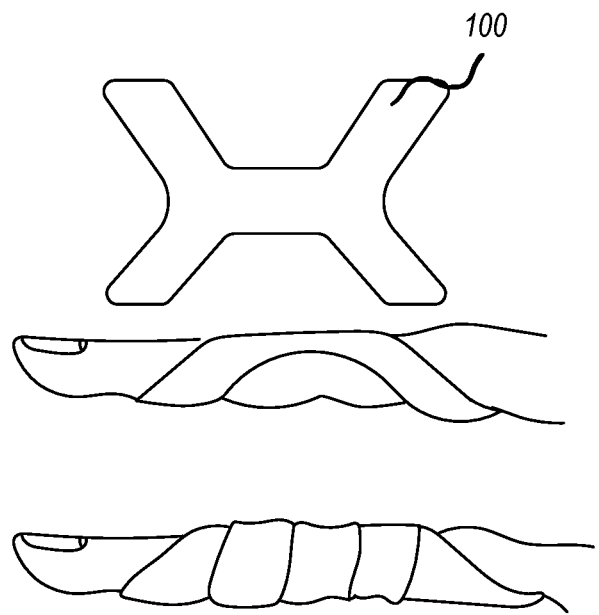
Figure 3F:
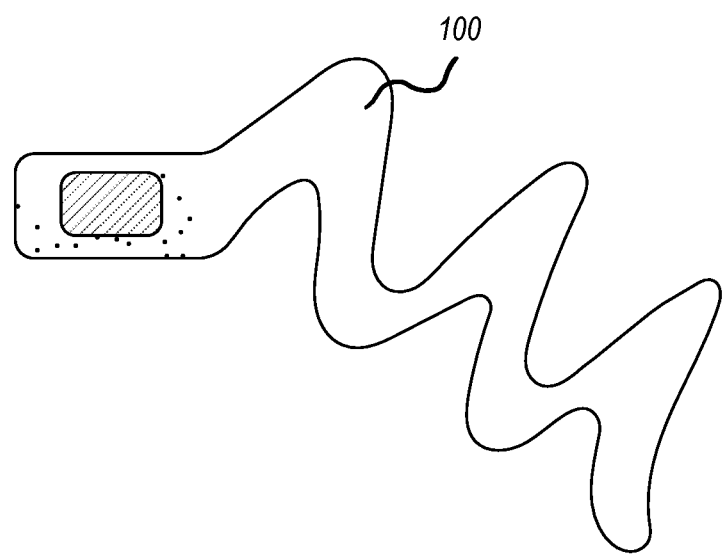
Figure 3G:
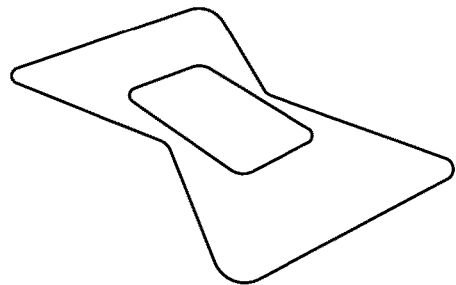
Figure 3H:
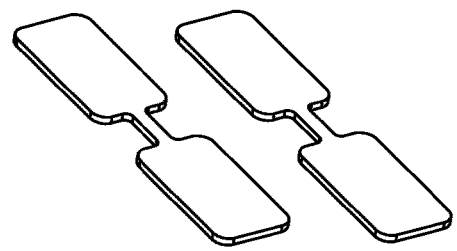
Figure 3I:
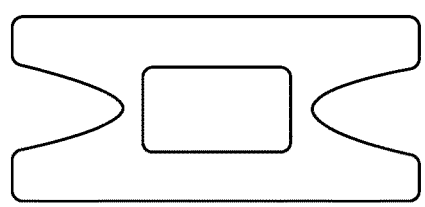
Figure 3J:
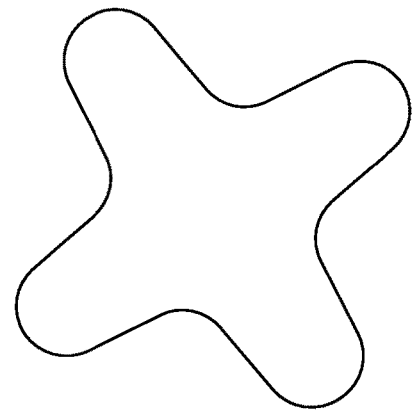
Figure 3K:
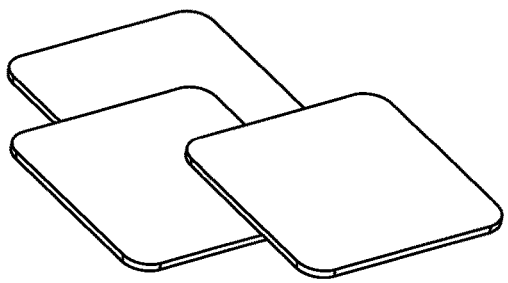
Figure 3L:
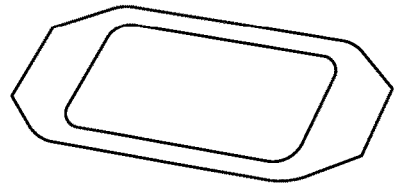

FIGS. 3E through 3L illustrate additional bandage types and configurations that may be utilized as semi-rigid bandages or in conjunction with semi-rigid bandages described herein. FIG. 3E, for example, illustrates a bandage type suitable for use on an extensor injury (e.g., a finger). FIG. 3F illustrates an exemplary dressing having a non-adherent roll portion and an adhesive portion at an end for closing/attaching the dressing to itself. FIGS. 3G through 3J illustrate various bandage shapes that may be utilized (e.g., butterfly, star, wedge-shaped) according to injury site, user needs, or preferences. FIG. 3K illustrates a foam dressing, and FIG. 3L illustrates a transparent dressing. Wound dressing types that may be utilized as semi-rigid bandages or in conjunction with semi-rigid bandages include, for example, gauze sponges, gauze bandage rolls, non-adherent pads, non-adherent wet dressings, foam dressings, alginates, and hydrogels.

Semi-Rigid Bandage Kits

Figure 4:
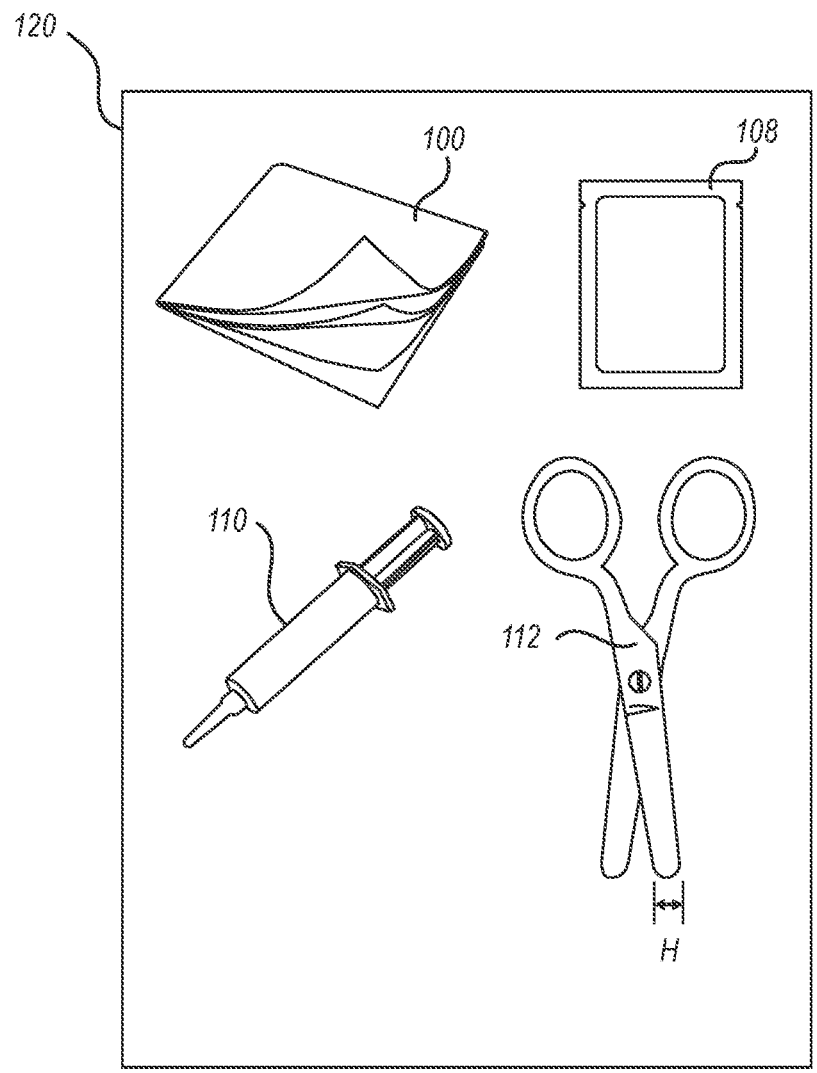
FIG. 4 illustrates an exemplary kit that includes the semi-rigid bandage material and optionally one or more additional components to assist in effective use of the semi-rigid bandage material.

FIG. 4 illustrates an embodiment of a kit 120 configured to enable a user to readily form a semi-rigid bandage. The kit 120 may include the semi-rigid bandage material 100 plus one or more of the additional illustrated components. That is, some of the other components may be optional depending on the intended use of the kit 120 and/or user needs or preferences. The kit 120 may additionally include other first-aid items known in the art. The kit 120 may be used as a general first-aid kit, wound-management kit, hiking kit, medical office kit, sports aid kit, or as a kit designed for any other application where it may be beneficial to apply a semi-rigid bandage. In some embodiments, the kit 120 is provided in a pre-packaged form. The packaging may have features that allow easy opening when desired, such as frangible seals, perforated tear lines, "pop" open features, and the like.

As shown, the kit includes the semi-rigid bandage material 100. The kit 120 may also include an activator 108 so that the user can readily apply an activation agent to the semi-rigid bandage material 100 to begin the hardening process. For example, where the semi-rigid bandage material 100 is water activated, the activator 108 includes sterile saline water, deionized water, or other suitable water source. The activator 108 may be provided in a pouch, capsule, tube, packet, satchel, sachet, or other suitable container.

The kit 120 may also include a tissue glue 110. Kits containing tissue glue 110 may be more applicable to a professional setting (e.g., doctor's office or emergency room). The tissue glue 110 may be beneficial in a wound-management kit, for example. In some instances, it may be beneficial to first close a wound using a tissue glue and then to apply a semi-rigid bandage on top of the glued wound. The glue can function to keep the wound locally closed while the semi-rigid bandage provides additional structural support to maintain wound closure and also acts as a protective barrier for the glue and the wound. The tissue glue 110 may include a cyanoacrylate glue (e.g., octyl or butyl esters such as octyl cyanoacrylate, n-butyl cyanoacrylate, isobutyl cyanoacrylate), fibrin glue, and/or other suitable tissue glues. The tissue glue 110 is preferably provided in a tube, syringe barrel, or other dispenser suitable for an adhesive.

The kit 120 may also include a cutting tool 112. The cutting tool 112 may be provided as a pair of safety, rounded-tip scissors 112, as shown. The cutting tool 112 may alternatively be provided as a knife, blade, cutting wire, or other cutting device capable of cutting semi-rigid bandages. As shown, the cutting tool 112 includes a blade with a height "H". The height H is preferably configured to be no greater than the thickness T of the padding layer 106. This enables the user to readily insert the cutting blade into the padding layer 106 between the skin and the bandage structure layer 102 to begin cutting the semi-rigid bandage.

Because the padding layer 106 will often compress somewhat once the semi-rigid bandage material 100 is applied, it is even more preferable that the height H be set somewhat smaller than the uncompressed thickness T of the padding layer 106 in order to compensate for expected compression. For example, the height H may be set at about 50% to about 95% of the uncompressed thickness T of the padding layer 106, or about 60% to about 90% of the uncompressed thickness T of the padding layer 106.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A kit for managing a wound or injury, comprising:
a cutting tool having a blade height; and
a semi-rigid bandage material, the semi-rigid bandage material comprising: a bandage structure layer;
a padding layer having a thickness disposed on a side of the bandage structure layer; and
a curable resin material embedded within the bandage structure layer, the curable resin material formulated to cure and thereby form a bandage,
wherein the bandage structure layer and curable resin material are configured such that when the curable resin material cures, the resulting bandage is semi-rigid, and
wherein the thickness of the padding layer is greater than the blade height of the cutting tool.

2. The kit of claim 1, wherein the bandage structure layer includes one or more of cotton, polyester, rayon, or blends thereof.

3. The kit of claim 1, wherein the bandage structure layer omits fiberglass.

4. The kit of claim 1, wherein the curable resin material is formulated to activate in the presence of air.

5. The kit of claim 1, wherein the curable resin material is formulated to activate in the presence of water.

6. The kit of claim 1, wherein the curable resin material includes a polyurethane prepolymer.

7. The kit of claim 1, wherein the semi-rigid bandage material further comprises an embedded antimicrobial agent.

8. The kit of claim 1, wherein the semi-rigid bandage material further comprises one or more embedded analgesics, anesthetics, or clotting factors.

9. The kit of claim 1, wherein the resulting bandage has a Shore A hardness of about 40 to about 100.

10. The kit of claim 1, wherein the resulting bandage has a Young's modulus of about 0.5 to about 3.5 GPa.

11. The kit of claim 1, wherein the padding layer is formed from a different material than the bandage structure layer.

12. The kit of claim 1, wherein the padding layer omits an embedded resin material.

13. The kit of claim 1, further comprising one or more of:
an activator in a container; or
a tissue glue in a dispenser.

14. The kit of claim 13, wherein the tissue glue comprises cyanoacrylate and/or fibrin glue.

15. The kit of claim 1, wherein the cutting tool is a pair of round-tipped scissors.

16. A method of managing or preventing a wound or injury, comprising:
providing the kit as in claim 1;
applying the semi-rigid bandage material to an injury site or a target site to prevent injury at the target site; and
allowing the semi-rigid bandage material to harden into a semi-rigid state.

17. The method of claim 16, wherein the injury site is a wound, cut, or laceration.

18. The method of claim 17, wherein a tissue glue is first added to the wound, cut, or laceration, and wherein the semi-rigid bandage material is applied over the tissue glue.

19. The method of claim 16, wherein the target site is a joint, and wherein the semi-rigid bandage material is applied to the joint to prevent injury at the joint.

\* \* \* \* \*